United States Patent [19]

Rehn et al.

[11] 4,018,819
[45] Apr. 19, 1977

[54] PROCESS FOR THE MANUFACTURE OF 2-CHLOROETHANE-PHOSPHONIC ACID

[75] Inventors: Karl Rehn, Hofheim, Taunus; Otto Schaffner, Morfelden; Gerhard Stähler, Frankfurt am Main, all of Germany

[73] Assignee: Hoechst Aktiengesellschaft, Frankfurt am Main, Germany

[22] Filed: Aug. 19, 1975

[21] Appl. No.: 605,868

Related U.S. Application Data

[63] Continuation of Ser. No. 207,620, Dec. 13, 1971, abandoned.

[30] Foreign Application Priority Data

July 9, 1971   Germany ........................... 2134346

[52] U.S. Cl. ........................................ 260/502.4 R
[51] Int. Cl.$^2$ ........................................ C07F 9/38
[58] Field of Search ............................ 260/502.4 R

[56] References Cited

UNITED STATES PATENTS 3,787,486   1/1974   Randall et al. ............. 260/502.4 R
3,808,265   4/1974   Randall et al. ............. 260/502.4 R

FOREIGN PATENTS OR APPLICATIONS 1,565,742   3/1959   France ....................... 260/502.4 R

OTHER PUBLICATIONS

Kabachnik et al., "Chem. Abstracts", vol. 42 (1948), cols. 7241–7243.
Luder et al., "General Chemistry", (1959), pp. 169–182.

Primary Examiner—Joseph E. Evans
Attorney, Agent, or Firm—Curtis, Morris & Safford

[57] ABSTRACT

An improved process for the manufacture of 2-chloroethane phosphonic acid in which 2-chloroethane phosphonic acid bis(2-chloroethyl)-ester is heated with excess hydrogen chloride in the presence of 0.1 to 31% by weight of water at temperatures above 100° C under pressure, the 1,2-dichloroethane formed during the reaction is continuously or discontinuously distilled off and the decrease in pressure is compensated by adding gaseous hydrogen chloride.

7 Claims, No Drawings

PROCESS FOR THE MANUFACTURE OF 2-CHLOROETHANE-PHOSPHONIC ACID

This is a continuation of application Ser. No. 207,620 filed Dec. 13, 1971, now abandoned.

The present invention relates to a process for the manufacture of 2-chloroethane-phosphonic acid.

2-Chloroethane-phosphonic acid is of industrial importance as ripening promotor and growth regulator as well as intermediate for the manufacture of polyvinylphosphonic acid used in corrosion protection.

Processes for the manufacture of 2-chloroethane-phosphonic acid and its precursors have been described in German Pat. No. 1,123,667 and French Pat. No. 1,558,691; furthermore by Kabachnik et al. (Chem. Abstr. 42, 7241-43), French Pat. No. 1,565,742 and German Application 1,815,999 laid open to public inspection.

The most economic process from among the three former publications appears to be the three step process disclosed by Kabachnik et al. and carried out according to the following scheme:

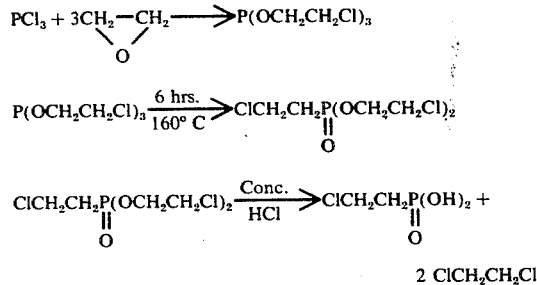

2 ClCH$_2$CH$_2$Cl owing to the fact that the starting products phosphorus trichloride and ethylene oxide are cheap industrial products. However, according to Kabachnik, in the first stage 10 to 20% and in the second stage more than 50% of a non-distillable residue are formed. Although this amount of residue could be reduced by carrying out the reactions in suitable solvents this would require in both steps costly distillations under strongly reduced pressure and at elevated temperature. In the third step Kabachnik et al. describe the hydrolysis of the pure 2-chloroethane-phosphonic acid bis-(2-chloroethyl) ester by means of concentrated hydrochloric acid but with partial success only. The reaction product must therefore be subjected, after distillation of the excess hydrochloric acid, to further purification operations to obtain a product of satisfactory purity.

In further developing the aforesaid process French Pat. No. 1,565,742 describes the rearrangement of tris-(2-chloroethyl)-phosphite in high boiling solvents, for example o-dichlorobenzene, cumene or xylene, at 150 to 160° C. The phosphonate obtained is hydrolized, without further purification, with gaseous hydrogen chloride or 20% aqueous hydrochloric acid. When a large excess of hydrogen chloride is passed through for several hours a mixture is formed which, according to Example 1 of German Application 1,815,999 cited above, contains approximately 30% of 2-chloroethane-phosphonic anhydride besides 2-chloroethane-phosphonic acid. The reproduction of Example 2 of the French Patent (hydrolization of the product by boiling it for 90 hours with 20% hydrochloric acid), yielded a nonsolidifying oil. Trimethylsilylation and subsequent gas chromatography of this oil showed that it contained 0.5% of starting material, 8% of 2-chloroethane-phosphonic acid mono(2chloroethyl) ester, 40% of 2-chloroethane-phosphonic acid and 8.9% of 2-hydroxyethane phosphonic acid besides further constituents that could not be determined in this manner. The necessity of isolating the 2-chloroethane-phosphonic acid from the partially hydrolized reaction mixture and from the anhydride makes the process of the French patent uneconominic.

Our copending Application Serial No. 207,619 (HOE 70/F 280K) filed concurrently with out patent application and now abandoned describes a process for the manufacture of 2-chloroethane-phosphonic acid by cleavage of 2-chloroethane-phosphonic acid bis(2-chloroethyl) ester, which comprises carrying out the cleavage with 50 to 500% by weight of aqueous hydrochloric acid at a temperature above 100° C under elevated pressure, distilling off the 1,2-dichloroethane formed during the reaction either continuously or discontinuously, and compensating the fall in pressure during the reaction by adding gaseous hydrogen chloride.

It has now been found that the cleavage of the crude 2-chloroethane-phosphonic acid bis(2-chloroethyl) ester can also be carried out with excess hydrogen chloride in the presence of small amounts of water, i.e. 0.1 to 31% by weight of water, corresponding to about 0.2 to less than 50% by weight of concentrated hydrochloric acid, calculated on the amount of crude product to be hydrolyzed.

To carry out the hydroylsis the crude chloroethane-phosphonic acid bis(2-chloroethyl) ester is heated with hydrochloric acid in an amount as defined above at a temperature above 100° C, preferably above 120° C in an autoclave resistant to hydrochloric acid while stirring. The purity of the final product decreases with increasing temperature so that the hydrolysis should not be carried out at a temperature above 200° C. In order to maintain always an excess amount of HCl in the autoclave, the NCl deficiency resulting from the use of small amounts of aqueous hydrochloric acid is compensated by adding gaseous hydrogen chloride. In the reaction vessel a pressure in the range of from 1 to 10 atmospheres gauge, preferably 3 to 6 atmospheres gauge, is maintained if necessary by forcing in hydrogen chloride. The dichloroethane formed is repeatedly distilled off by releasing the overpressure. The escaping hydrogen chloride and the hydrogen chloride used up by the reaction are replenished by forcing in again hydrogen chloride. When the reaction vessel is connected with a collecting vessel by means of a closed reflux condenser the dichloroethane can be removed continuously, whereby losses of hydrogen chloride are avoided.

At a temperature of 130° C, for example, the hydrolysis is terminated after approximately 4 hours. The aqueous hydrochloric acid which still contains small amount of 2 -chloroethanol is distilled of at 20° – 100° C under reduced pressure.

In the process according to the present invention the desired 2-chloroethane-phosphonic acid is obtained practically pure and with excellent yields. The reaction can be performed with pure starting compound as well as with a nonpurified product as obtained by the reaction of ethylene oxide with phosphorus trichloride with subsequent rearrangement of the tris(2-chloroethyl)-phosphite formed to the corresponding phosphonate.

The following Examples illustrate the invention.

EXAMPLE 1:

In a 4 liter flask provided with stirrer and thermometer and connected with a reflux condenser and separator with discharge cock 2.05 kilograms of ethylene oxide were introduced into a mixutre of 2.055 kilograms (15 moles) of phosphorus trichloride and 0.4 kilogram of chlorobenzene while stirring and cooling at 25° – 35° C during the course of 3 4 hours in a manner such that the ethylene oxide was fully absorbed. Stirring of the reaction mixture was continued for 3 hours at 30° – 40° C, then the chlorobenzene was distilled off while heating until the temperature had reached 155° – 160° C.

The cock at the separator was closed and heating was continued so that the chlorobenzene boiling with reflux maintained the temperature of the reaction mixture at 155° – 165° C. When the reaction temperature dropped below 150° C owing to the refluxing 1,2-dichloroethane formed in the reaction, the discharge cock was opened and the dichloroethane was distilled off until a temperature of 155° – 165° C had been reached again. After 5 to 6 hours the solvent together with the residual dichloroethane were distilled off, finally under a slightly reduced pressure. 3590 Grams of an almost colorless oil containing about 50% of non-distillable constituents were obtained.

The crude 2-chloroethane-phosphonic acid bis(2-chloroethyl) ester thus obtained was introduced together with 150 grams of concentrated hydrochloric acid in an enamelled autoclave having a capacity of at least 3 liters provided with an inlet through the cover connected with a hydrogen chloride bomb and an outlet connected with a condenser via a valve. In the autoclave a pressure of 1 atmosphere gauge was produced by forcing in hydrogen chloride. The reaction mixture was then heated at 130° – 140° C and the intially increasing but then dropping pressure - owing to the consumption of hydrogen chloride - was maintained at 3 to 6 atmospheres gauge by forcing in hydrogen chloride. After one hour the dichloroethane formed was distilled off by opening the valve to the condenser. When the valve was closed again the fallen pressure was increased to 3 to 5 atmospheres gauge by forcing in hydrogen chloride and while heating. This procedure was repeated at 1 hour's intervals until no more dichloroethane distilled off. The reaction mixture was maintained for a further 3 hours under a hydrogen chloride pressure of 3 to 5 atmospheres gauge and at 130° – 140° C. After the temperature had been reduced to 100° C the hydrogen chloride was removed from the autoclave by opening the valve. Hydrochloric acid and residual dichloroethane were distilled off under a pressure of 2 to 40 mm of mercury. 2050 Grams of 2-chloroethane-phosphonic acid were obtained have a solidification point of 62° – 66° C. Gas chromatographic analysis carried out as described above indicated a content of 93 to 95% of 2-chlorethane-phosphonic acid besides 5 to 7% of phosphoric acid, corresponding to about 90% of 2-chloroethane-phosphonic acid, calculated on the phosphorus trichloride used.

EXAMPLE 2:

The procedure of Example 1 was repeated with the exception that the hydrolysis of the ester was carried out with 90 grams of water instead of 150 grams of concentrated hydrochloric acid. The result obtained was the same.

EXAMPLE 3:

Tris(2-chloroethyl)-phosphite prepared from 50 kilograms of phosphorus trichloride and 50 kilograms of ethylene oxide was rearranged to the phosphonic acid ester by heating it for several hours at 160° – 170° C in a 100 liter enamelled vessel provided with stirrer and an enamelled reflux condenser connected with a separator. After distillation of the dichloroethane the outlets of the reflux condenser and separator were closed. At a temperature of from 130° to 140°C an internal pressure of 3 to 6 atmospheres was produced by forcing in gaseous hydrogen chloride. After the addition of hydrogen chloride 4 liters of water were introduced into the vessel. The cleavage set in and the dichloroethane formed was distilled off by opening the connection between the reflux condenser and the separator. The pressure in the reaction vessel which decreased owing to the consumption of hydrogen chloride was maintained at 3 to 6 atmospheres gauge by forcing in hydrogen chloride at 130° – 140° C until the formation of dichloroethane was terminated after 15 to 20 hours. The reaction mixture was then maintained at 130° – 150° C for a further 3 hours under a hydrogen chloride pressure of 3 to 6 atmospheres gauge.

After distilling off the aqueous hydrochloric acid under a slightly reduced pressure 52 kilograms of crude 2-chloroethane-phosphonic acid having a solidification point of 62° – 64° C were obtained. The product consisted of 93 to 97% of pure 2-chloroethane-phosphonic acid besides 3 to 7% of phosphoric acid.

EXAMPLE 4:

Tris(2-chloroethyl)-phosphite obtained from 56 kilograms of phosphorus trichloride and 56 kilograms of ethylene oxide was rearranged to the 2-chloroethane-phosphonic aicd bis(2-chloroethyl) ester by heating it for 6 hours at 155° – 165° C in the presence of 22 kilograms of chlorobenzene in an enamellined autoclave having a capacity of 150 liters and provided with stirrer, heating jacket and reflux condenser connected with a collecting vessel via a cock. The chloroebenzene was removed by distillation and 5 kilograms of concentrated hydrochloric acid were added. Next, the openings of the autoclave were closed and hydrogen chloride was introduced to increase the internal pressure to 1 atomsphere gauge. The reaction mixture was heating at 130° – 140° C. The pressure which increased initially and then dropped owing to the consumption of hydrogen chloride was maintained at 3 to 5 atmospheres gauge by forcing in hydrogen chloride. At intervals of about 1 hour dichloroethane was distilled off as described in Example 3 and hydrogen chloride was forced in. The formation of dichloroethane was terminated after 8 – 10 hours. The reaction mixture was heated for another 3 hours at 130 – 140° C under a hydrogen chloride pressure of 3 to 5 atmospheres gauge After removal of excess hydrogen chloride and distillation of hydrochloric acid under a slightly reduced pressure 53 kilograms of 2-chloroethane-phosphonic acid having a solidification point of 62° to 66° C remained behind. The product had a degree of purity of 94 to 97% and contained 3 to 5% of phosphoric acid. In the reaction 45 to 50 kilograms of hydrogen chloride were consumed.

EXAMPLE 5:

The procedure of Example 3 was repeated with the exception that in the third reaction stage an enamel-lined steel reflux condenser and collecting vessel withstanding a pressure of 6 atmospheres gauge were used to that from the closed system the formed dichloroethane could be continuously distilled off. With otherwise identical reaction conditions only 30 kilograms of hydrogen chloride were consumed, giving the same yield of 93 to 97% of pure 2-chloroethane-phosphonic acid.

What is claimed is:

1. In a process for the manufacture of 2-chloroethane-phosphonic acid by the hydrolytic cleavage of 2-chloroethane-phosphonic acid-bis(2-chloroethyl) ester by contacting said ester with hydrogen chloride in the presence of 0.1 to 31 percent of water, by weight of said ester, at a temperature above 100° C. and under an elevated pressure and maintaining an elevated pressure during the reaction by adding gaseous hydrogen chloride, the improvement which comprises distilling off during the reaction to 1,2-dichloroethane formed by the reaction.

2. The process of claim 1, wherein hydrochloric acid having a concentration of from 30 to 38% by weight is used for the cleavage.

3. The process of claim 1, wherein a pressure of from 1 to 10 atmospheres gauge is maintained during hydrolysis.

4. The process of claim 3, wherein the pressure is 3 to 6 atmospheres gauge.

5. The process of claim 1, wherein the hydrolysis is carried out at a temperature of from 110° to 190° C.

6. The process as in claim 1, wherein 1,2-dichloroethane is distilled off discontinuously.

7. The process as in claim 1, wherein 1,2-dichloroethane is distilled off continuously.

* * * * *